United States Patent [19]

Stofer

[11] Patent Number: 5,616,619
[45] Date of Patent: Apr. 1, 1997

[54] TOPICAL COMPOSITION FOR BURN RELIEF AND METHOD OF USE

[76] Inventor: Dorothy E. Stofer, 5331 Lake LeClare Rd., Lutz, Fla. 33549

[21] Appl. No.: 244,545

[22] PCT Filed: Mar. 15, 1994

[86] PCT No.: PCT/US94/02787

§ 371 Date: Jun. 3, 1994

§ 102(e) Date: Jun. 3, 1994

[51] Int. Cl.$^6$ ............................................. A61K 31/19
[52] U.S. Cl. ........................... 514/574; 424/DIG. 13; 514/938
[58] Field of Search .................... 424/DIG. 13, 195; 514/938, 574

[56] References Cited

U.S. PATENT DOCUMENTS

| | | | |
|---|---|---|---|
| 624,925 | 3/1890 | Grapewine | 424/62 |
| 1,990,676 | 2/1935 | Stern | 514/938 |
| 2,143,751 | 1/1939 | Chase | 429/DIG. 13 |

FOREIGN PATENT DOCUMENTS 901624  7/1962  United Kingdom ................ 8/160

OTHER PUBLICATIONS

The Merck Index, 1976, p. 1111.
Cosmetic Materials, 1963, vol. 2, pp. 432 and 433, Harry.

*Primary Examiner*—Shelley A. Dodson
*Attorney, Agent, or Firm*—Dominik & Stein

[57] ABSTRACT

A topical composition for treatment of skin burn, comprising salt and lemon juice, preferably in proportions sufficient to form a pasty composition. A method for treatment of skin burn using this topical composition is also disclosed.

17 Claims, No Drawings

TOPICAL COMPOSITION FOR BURN RELIEF AND METHOD OF USE

BACKGROUND OF THE INVENTION

1. Field of the Invention

This invention relates to topical compositions and methods of using them for reducing pain and promoting healing of burn related wounds.

2. Description of the Related Art

Skin is the largest organ of the body, and performs a critical function as a protective waterproof covering for the entire body. Skin contains many sensory nerve endings which keep us informed regarding our external environment, as well as myriad blood vessels which aid in temperature regulation. Skin is modified for different areas of the body, and forms a thick, heavy epidermis on the palms of the hand and palms of the feet, as compared to the thin layer over the rest of the body.

Skin is composed of two layers. The outer layer, the epidermis, contains several layers of stratified epithelial cells, with increasing amounts of protein keratin in the outermost layers. This arrangement decreases excessive water loss from the skin surface and renders the body relatively insensitive to minor abrasions and injuries. Furthermore, the epidermis has a limited distribution of nerve endings and is devoid of blood vessels so that one can shave off several layers of cells without blood loss or pain.

The stratum germinativum is the innermost layer of the epidermis and contains several layers of cells undergoing mitosis. The stratum corneum is the outermost layer of the epidermis, and makes up most of the epidermis. The flattened, dehydrated cells of the stratum corneum are constantly flaking off, often in irregular patches, for instance, after sunburn, and are replaced by cells migrating towards the surface from the deeper epidermal layers. The dead cells provide an effective covering which protects the entire body against water loss and is also a poor conductor of heat. Thus, brief contact with a hot object does not burn the skin.

However, longer contact with hot objects can result in destruction of skin and in vascular damage. While the body is capable of regenerating skin and healing minor burn related wounds without medical attention, more substantial burns require first-aid or even medical attention.

Of the injuries to the skin, burns are perhaps the most painful, and so treatment of skin burns involves not only treatment to expedite healing, but also treatment to reduce or control pain. Skin injuries are difficult to treat due to the constant exposure of the skin to the dehydrating effect of the aerobic environment and to movement. A further concern with burn related wounds is the increased susceptibility to infection. Severe skin burns largely diminish the protective mechanisms of skin against infection, and leave necrotic tissue.

In the past, skin burns have been covered with dressings such as salves, vaseline, and fibrous or synthetic polymer bandages, in an effort to prevent dehydration, protect against heat loss, prevent bacterial infection, and to maintain a moist environment about the wound to facilitate debridement. Conventional bandages are made of materials such as natural or synthetic fibers. One problem with such conventional covers is that, as the skin exudes serum an pus, this exudate is absorbed by the bandage. This proteinaceous material provides a culture medium for bacteria. Further, as the exudate hardens, the bandage is likely to become adhered to the skin. As the bandage is removed, the scab is also frequently removed. This can be extremely painful.

Various compounds have been developed as an alternative to, or for use with, bandages. For example, U.S. Pat. No. 85,385 (Hughes) teaches a medicinal compound suitable for treatment of skin ailments including burns, which composition is made by mixing and simmering cider-vinegar, molasses, spirits of turpentine, salt, saltpeter, oil of vitriol, and olive oil.

U.S. Pat. No. 321,839 (Neuer) teaches a medicinal compound for treatment of skin wounds, comprising thymol, boracic acid, potassium chloride, sodium chloride, and oil of wintergreen.

U.S. Pat. No. 390,534 (Tomlinson) teaches a lotion for treatment of sores, wounds and the like, comprising water, gambier extract, salt, and sulphuric acid.

Recently improvements have been made in bandages by the provision of a thin perforated non-adhering plastic film between the bandage and the wound. However, exudate remaining between the plastic and the wound, and this provides an excellent medium for bacterial proliferation.

Even more recently a new class of bandages has been developed of natural or synthetic materials which are water swellable, i.e., they absorb water without dissolving in water.

Exemplary of these is U.S. Pat. No. 4,732,755 (Grana), which teaches the application of sodium polyacrylate powder as a dressing over the skin burn area, and wetting the powder such as by spraying with distilled water, until the powder becomes moist. The outer wetted surface of the moistened powder dries to form a parchment like surface, and may remain in place for 2–3 weeks.

U.S. Pat. No. 4,837,019 (Georgalas et al.) teaches a skin treatment composition for treating burned skin, which composition is capable of counteracting moisture loss and promote healing, and which comprises a moisturizing component formed of polyglycerylmethacrylate, glycerine, allantoin, panthenol, amino acid complex, and fibronectin.

U.S. Pat. No. 5,009,890 (DiPippo) discloses a burn treatment product in the form of a water-soluble, biodegradable gel, the active ingredients of which are water and Tea Tree Blend. A gum material is used to maintain the water and Tea Tree Blend in a gel state.

A number of compositions have been developed for the treatment of skin burns, but these compositions contain medications which are expensive and not readily available.

In each case discussed above, the composition is either expensive or is formulated from ingredients which is not readily available. Further, the application of various of the prior art compositions to a burn may require medical training and constant attention. Further, various patients may have reactions to certain of the non-naturally occurring pharmaceutical compositions.

In view of the foregoing, it is an object of the present invention to provide a topical composition for treatment of skin burns which eliminates or minimizes the above-mentioned and other problems, limitations and disadvantages typically associated with conventional topical compositions, and to provide a topical composition which is inexpensive, easily obtainable, simple to manufacture, easy to apply and use, reliable, storage-stable, and which does not necessarily require medical training to use.

SUMMARY OF THE INVENTION

After extensive investigation and experimentation, the present inventor has discovered that the objects of the invention can be simply, eloquently, and inexpensively accomplished by a topical composition for the treatment of burns comprising a mixture of one part lemon juice to sufficient salt to form a pasty, plastic, formable composition (usually about 2 to 2.5 parts salt), which topical composition can be applied directly to the affected area of the skin without the need for complicated medical diagnosis, pretreatment, and monitoring. The composition stops pain on contact, prevents blistering, causes the tissue to remain elastic, promotes healing and prevents infection.

DETAILED DESCRIPTION OF THE INVENTION

The present invention more specifically concerns a topical composition and method for treatment of traumatized skin, i.e., thermal burns ranging from mild injury to extensive necrosis of the skin and/or underlying tissues. The composition and method not only expedites the healing of first and second degree burns, which are normally capable of healing without scarring, but also promotes the healing of third degree burns without scar tissue.

The ability to heal third degree burns without scarring is important not only for the treatment of accidental burns, but also in the treatment of intentional burns, such as thermal burns for destruction of birthmarks, disfiguring scars resulting from earlier injury, and the like.

The composition of the present invention is capable of application to mammals in general and humans in particular.

This invention is particularly useful when applied to traumatized tissue immediately after injury, but may also be applied one or more days after injury. Healing begins promptly upon application of the composition to the affected area, and the duration of healing will vary, depending upon the extent of the injury, from a few days to a few weeks.

The salt patch may be removed and changed without fear of adhesion to the skin as in the case of fabric-based bandages. Alternatively, the salt patch may remain in place until sloughed off by the growth of new tissue under the new tissue under the bottom layer of the protective layer.

In addition to reducing pain and promoting healing, it is believed that both the salt concentration in the patch and the citrus juice or citric acid thereof act as excellent anti-bacterial and anti-viral agents, preventing infection of the skin.

It has been known to use various citrus juices in relationship with the skin. For example, U.S. Pat. No. 5,083,208 teaches a method of massage with 10–15% lemon oil and 85–90% lemon juice, but cautions that the astringency of the lemon juice may cause minor irritation to abrasions and open wounds, and recommends flushing wounds with water in case the composition contacts wounds. U.S. Pat. No. 5,152,000 teaches a hair grower consisting of extract of skin of naval orange, skin of iyokan (Citrus iyo), skin of hassaku (Citrus hassaku), the skin of sweet summer orange, the skin of lemon, the skin of mandarin orange, and aloe, all of which extracts are prepared by extracting with sake.

An investigation of the virucidal activity of organic acids, including citric acids, against various groups of viruses can be found in Poli et al "Virucidal Activity of Organic Acids" Fd Chem (1979), pages 251–258. The organic acids being tested are mixed into a viral suspension. There is no suggestion for combination with salt, and there is no suggestion that organic acids can be applied to skin burn to prevent infection and promote healing.

On the other hand, it is known to use salt in treatment of various conditions of the skin. U.S. Pat. No. 711,263 (Robertson) discloses a composition for remedy of diseases of the skin, comprising magnesium chloride, sodium chloride, potassium chloride, magnesium sulfate, magnesium bromide, and acetic acid.

U.S. Pat. No. 3,579,632 (Sonnen) teaches a hair and scalp treatment with a sodium chloride thick viscous aqueous slurry.

U.S. Pat. No. 3,574,854 describes the application of a composition containing a solution of 10 to 15 percent sodium chloride in a soothing base for the purpose of soothing skin.

U.S. Pat. No. 3,867,522 (Kligman) discloses a composition for treatment of acne, which composition comprises sodium chloride crystals in 30 to 60 percent concentration in a suitable vehicle or base which acts as a carrier. The composition is applied to the affected skin in such a manner as to debride the lesions and comedos which are characteristic of acne.

U.S. Pat. No. 4,608,044 (Nordquist et al) teaches a compress for treatment of wounds, which compress is designed for delivering salt to the wound.

Recently, a wound gel composition has been developed containing sodium chloride. See U.S. Pat. No. 5,271,943 (Bogart et al). Therapeutic gels are disclosed comprised of water, sodium chloride, and a gelling agent. This patent also presents a detailed discussion of the state of the art treatment of wounds with gel compositions and/or salt containing compositions, the entirety of which is incorporated herein by reference.

However, it has never, prior to the making of the present invention, been attempted to treat skin burns with a concentrated combination of salt and citrus juices.

The topical composition of the present invention is prepared by mixing 1 part lemon juice with about 2 to 2.5 parts salt. The salt may be any pharmaceutically acceptable, topically tolerable salt, but most preferred for reasons of cost and availability is common table salt (sodium chloride). The salt may include minor amounts of sodium iodide and potassium chloride as found in common table salt. Other ingredients or modifiers may be added, so long as they do not substantially effect the therapeutic effect of the combination of salt and lemon juice. The product should be a pasty composition which can be easily applied to the skin and held in place by a gauze bandage.

The citrus juice may be obtained from any citrus fruit, such as lime juice, lemon juice, orange juice, pink grapefruit juice, regular grapefruit juice, sour orange juice, tangerine, tangelo, etc. but is preferably lemon juice. The lemon juice is most preferably freshly squeezed lemon juice, but where such is not available, may be reconstituted lemon juice.

The composition may be premixed and stored in the premixed state. The composition is storage stable in a refrigerator and maintains it's activity for months. As an alternative to premixing, it is possible to apply salt directly to a traumatized area of the skin and to squeeze a lemon over the salt so that the lemon juice wets the salt.

It has been found that the salt has little effect on the burn independently of the citrus juices, but when combined with the citrus juices an unexpected healing effect occurs. It has not been confirmed whether the effect is due to the moistening, acidifying, or salinity, but the surprising healing effect has been documented. Depending upon the intensity of the burn, the amount of composition to be applied may vary, but generally the composition is shaped and applied to a thickness of about ½ inch. The composition is held in place with gauze, and additional lemon juice is applied to the area of the gauze over the burn being treated so that the gauze is very moist. The composition of the present invention has it's greatest effect during the first part of the healing process, immediately after the injury. It is thus preferred to apply the composition to the injury as soon as possible after the trauma to the skin. The composition should be held in place for at least 2 to 3 days for severe trauma, but after the first few days treatment with the composition may be discontinued and the healing process allowed to continue with only conventional gauze bandages.

An advantage of the composition of the present invention is the feature that the composition is plastic and deformable, and thus can conform to the superficial contours of the wound.

EXAMPLES

In each of the following examples a composition was prepared by mixing approximately ¾ cup (6 ounces) of lemon juice or the equivalent thereof with 15 ounces of common table salt. There is no particular restriction on the manner of mixing, and common kitchen implements can be used. In each of the following examples the composition was applied to a thickness of about one half inch and wrapped with gauze, after which the gauze was wetted with lemon juice.

Example 1

A female in her early 20's was severely burned over the entire palm of her hand when a matchbook ignited in her hand. The composition of the present invention was formed into a patch and applied within two hours, and kept in place for approximately one week. The patch was changed once every morning and once every evening. The pain was reduced immediately, the composition giving a cooling sensation. The palm healed completely, with no scarring.

Example 2

While ironing clothes, an iron fell over onto the back of the hand of a small girl. The iron was immediately pulled away with concomitant removal of skin. The composition was applied and kept in place until the skin surrounding the wound turned white. Thereafter the wound was examined, and a fresh patch of the composition of the invention was applied. After one week the treatment was discontinued, and after three weeks the wound had healed, and after one year no scar can be seen on the hand.

Example 3

A chemical charge used to weld pipes was ignited and burned through a leather glove and into the back of the hand of an approximately 35 year old welder. The wound was only the size of a penny, but formed a rather deep third degree burn. The composition described above was applied to the back of the hand for a period of over 14 days, after which treatment was discontinued. Pain was controlled, and the wound healed completely, leaving almost no scar.

Example 4

While working on a truck, a watch worn on the wrist of 55 year old mechanic caused a short circuit between two truck batteries. The short circuit immediately heated the watch and severely burned the wrist of the mechanic. The composition of the invention was applied for 19 days, after which treatment was discontinued. The wound healed leaving almost no scar.

A number of other burns were treated, including gasoline burns, grease burns, and stove burns, using the same composition described above. All healing occurred with minimum of pain and minimum or complete absence of scarring.

Although the topical composition of the present invention was first designed for treatment of thermal burns, and thus is particularly suited for such treatments, it will be readily apparent that the system is capable of application to related conditions of the skin, such as acid burns, radiation burns, etc., and is thus capable of use in a number of other applications. Although this invention has been described in its preferred form with a certain degree of particularity with respect to treatment of thermal burns, it is understood that the present disclosure of the preferred form has been made only by way of example and that numerous changes in the details of ingredients of the composition and the manner of application to an injury may be resorted to without departing from the spirit and scope of the invention.

Now that the invention has been described,
What is claimed is:

1. A pasty, formable topical composition for treatment of burns of the skin consisting essentially of a mixture of citrus juice and salt, wherein said salt is a pharmaceutically acceptable, topically tolerable salt present in an amount of from 1.0 to 4.0 parts by weight per part by weight of citrus juice.

2. A topical composition as in claim 1, wherein said salt is sodium chloride.

3. A topical composition as in claim 1, wherein said citrus juice is lemon juice.

4. A topical composition as in claim 3, wherein said lemon juice is freshly squeezed lemon juice.

5. A topical composition as in claim 1, wherein said trauma is skin burn.

6. A topical composition as in claim 1, wherein said salt is present in an amount of from 1.5 to 2.5 parts by weight per part by weight of citrus juice.

7. A topical composition as in claim 1, wherein said citrus juice is selected from the group consisting of lime juice, lemon juice, grapefruit juice, orange juice, tangerine juice, and tangelo juice.

8. A topical composition for treatment of skin burns, consisting essentially of a mixture of citrus juice and salt, wherein said salt is present in an amount of from 1.0 to 4.0 parts by weight per part of citrus juice, and wherein said salt is present in an amount sufficient to form a pasty, formable, plastic composition with said citrus juice.

9. A topical composition consisting of citrus juice and salt for treatment of burns of the skin, wherein said salt is a pharmaceutically acceptable, topically tolerable salt present in an amount of from 1.0 to 4.0 parts by weight per part by weight of citrus juice, and wherein said salt and citrus juice together form a pasty, formable composition.

10. A topical composition as in claim 9, wherein said salt is sodium chloride.

11. A topical composition as in claim 9, wherein said citrus juice is lemon juice.

12. A topical composition as in claim 11, wherein said citrus juice is fresh squeezed lemon juice.

13. A topical composition as in claim 9, wherein said trauma is skin burn.

14. A topical composition as in claim 9, wherein said salt is present in an amount of from 1.0 to 4.0 parts by weight per part by weight of citrus juice.

15. A topical composition as in claim 9, wherein said salt is present in an amount of from 1.5 to 2.5 parts by weight per part by weight of citrus juice.

16. A topical composition as in claim 9, wherein said citrus juice is selected from the group consisting of lime juice, lemon juice, grapefruit juice, orange juice, tangerine juice, and tangelo juice.

17. A method for treatment of a skin burn, comprising applying to said skin burn a pasty and formable topical composition consisting essentially of citrus juice and salt, wherein said salt is a pharmaceutically acceptable, topically tolerable salt present in an amount of from 1.0 to 4.0 parts by weight per part by weight of citrus juice.

* * * * *